United States Patent
Maikner et al.

(12)

(10) Patent No.: US 7,049,394 B2
(45) Date of Patent: May 23, 2006

(54) METHOD FOR PREPARING FREE FLOW RESIN

(75) Inventors: John Joseph Maikner, Zionsville, PA (US); Marlin Kenneth Kinzey, Philadelphia, PA (US); James Charles Bohling, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 108 days.

(21) Appl. No.: 10/638,484

(22) Filed: Aug. 12, 2003

(65) Prior Publication Data

US 2004/0106774 A1 Jun. 3, 2004

Related U.S. Application Data

(60) Provisional application No. 60/404,402, filed on Aug. 19, 2002.

(51) Int. Cl.
*C08F 6/00* (2006.01)
*C08F 6/14* (2006.01)
*C08F 6/24* (2006.01)

(52) U.S. Cl. ............... 528/491; 528/492; 528/493; 528/494; 528/495; 528/496; 528/497; 528/498

(58) Field of Classification Search ............... 528/491, 528/492, 494, 495, 496, 497, 498
See application file for complete search history.

(56) References Cited

U.S. PATENT DOCUMENTS

| | | | |
|---|---|---|---|
| 4,330,672 A | * | 5/1982 | Hannon et al. ............ 528/493 |
| 4,904,715 A | | 2/1990 | Hunter et al. |
| 5,198,531 A | | 3/1993 | Webber et al. |
| 6,147,159 A | | 11/2000 | Hu et al. |
| 6,245,806 B1 | * | 6/2001 | Dombrowski et al. ...... 514/450 |
| 6,875,822 B1 | | 4/2005 | Ryoo et al. |

FOREIGN PATENT DOCUMENTS

| | | |
|---|---|---|
| DE | 2932321 | 2/1981 |
| JP | 62011740 | 1/1987 |

OTHER PUBLICATIONS

Su–Sun Wang, "p–Alkoxybenzyl Alcohol Resin and p–Alkoxybenzyloxycarbonylhydrazide Resin for Solid Phase Synthesis of Protected Peptide Fragments", Journal of the American Chemical Society, 95:4, Feb. 21, 1973, pp. 1328–1333.

Kenneth S. Cameron, et al., "Optimization of Reaction Conditions for REM Resin–Bound Quarternization Reactions", 2002 American Chemical Society, Mar. 7, 2002, pp. 199–203.

Sunil Rana, et al. "Influence of Resin Cross–Linking on Solid–Phase Chemistry", 2001 American Chemical Society, Dec. 14, 2000, pp. 9–15.

Harre, et al, "An efficient method for activation and recycling of trityl resins," Reactive and Functional Polymers, 1999, vol. 41, pp. 111–114, published by Elsevier Science.

* cited by examiner

*Primary Examiner*—James J. Seidleck
*Assistant Examiner*—Irina S. Zemel
(74) *Attorney, Agent, or Firm*—Carl P. Hemenway

(57) ABSTRACT

The present invention provides a method for producing a free flowing and/or non clumping resin that includes prior to drying, shrinking the resin under agitation. In one variant of the invention, the is a resin used in solid phase synthesis of peptides. In another aspect the invention provides a process of making a peptide using the free flowing resin described herein, and a polypeptide made using the process. Various therapeutics are then be made using the polypepdite.

7 Claims, No Drawings

METHOD FOR PREPARING FREE FLOW RESIN

CROSS REFERENCE TO RELATED PATENT APPLICATIONS

This is a non-provisional application of now abandoned U.S. provisional application Ser. No. 60/404,402 filed Aug. 19, 2002.

BACKGROUND OF THE INVENTION

Lightly crosslinked resins swell greatly when contacted with liquids which solvate the polymer chains For example polystyrene beads cross-linked with 1% DVB swell from 1.7 mL/g to over 6.5 mL/g when contacted with swelling solvents. This swelling makes the inside of the polymer bead more accessible and is often advantageous for washing the resin or performing chemistry on functional groups affixed to the resin. When the washings or chemistry has been completed one is often required to dry the resin. If resin is dried directly from the swollen state the resultant dry product often forms clumps or cluster of beads rather than the desirable free flowing material.

On a commercial or small scale when one dries directly lightly crosslinked resins, by way of example, 1% cross linked, styrene DVB resins (i.e. Merifield resins, CTC resins, unfunctionalized polystyrene, Wang resins, and resins useful for solid phase synthesis) after (1) being in any swelling solvent, e.g. after washing, clumps of beads form and the product becomes non-free flowing. As a result of this subsequent steps are made more difficult, and product performance is degraded. As a result of the clumping phenomenon, during subsequent processing beads on the outside of the clump become over functionalized while beads in the interior of the clump are underfunctionalized. For example, when CTC resins are made, when the resin is charged to a reactive acylating mixture, a mixture of undesirable products is obtained, i.e. dark beads are formed. These dark beads are over functionalized. When one builds a peptide one wants a uniform distribution of functional groups from bead to bead so that the growing peptide chains are not sterically constrained.

Some conventional solid phase synthesis products have the problem of simultaneous overfunctionalization and undefunctionalization as seen by microscopic analysis. There are beads that are inert and beads that are discolored indicating overfuntionalization.

There exists a need in the art to create a uniform distribution of beads with uniform bead to bead performance characteristics.

Another problem with the clumping phenomenon is that the conventional products clog feed tubes, funnels and other manufacturing components. This means that entire systems need to be shut down and cleanend or designed with larger components. There is a need in the art to create free flowing resins that do not clog manufacturing components.

In combinatorial chemistry, it is necessary to have uniform beads since any disparity in uniformity leads to unreliable results. Very small amounts of beads are placed into wells, and when one has over-functionalized or under-functionalized beads the results of the combinatorial study are not reliable.

Normally resins are shipped in bulk containers to end users. If the resins are not free flowing transfer of the bulk resin into manufacturing equipment is made difficult. There exists a need in the industry for free flowing resins that can be used in peptide synthesis and combinatorial synthesis. By way of further example, free flowing products are desirable when charging bulk resin from a bulk container for use in high throughput charging devices, e.g. those that spread materials through small apertures onto plates.

Conventionally, one dries a resin in a swollen state. One problem in following this procedure is that a large drier volume is necessary to dry the swollen resin. A second problem is that once the swollen resin is placed in the drier a much larger amount of solvent must be removed from the swollen resin resulting in longer drying times, and higher energy consumption. After all of these difficulties a lower quality, clumped resin is producted. There exists a need to solve these problems in the art.

Another difficulty is in transferring bulk resin to smaller retail packaging for laboratory uses. If the resin tends to clump, transferring and providing the desired weight accuracy is made more difficult. The resins sold are expensive to manufacture and thus have high selling prices. As such, it is necessary to accurately weigh and package amounts of resin so that the customer is provided the exact amount purchased. There exists a need in the art to provide a resin that is readily transferable from bulk containers into small, laboratory scale packages.

The art has attempted to create free flowing conditions by coating the beads with materials which prevent agglomeration. This method employs materials such as glycerol monostearate and glycerol disterate which persist on the bead after drying. See, DE 2932321. Similar methods,as disclosed in JP 62011740 A2, involve the use of nonionic surfactants such as polyoxyethylenenonylphenyl ether. These patents do not teach or fairly suggest swelling or washing and rely on residues being retained on the beads for their efficacy.

Washing the resins with swelling solvents is known to those skilled in the art. Cameron et. Al (J. Comb. Chem. 2002, 4, 199–203) relates to the use of methanol as a final wash solvent. The resin in this disclosure is a polar quaternary amine which is solvated and swollen by methanol. A similar example can be found in U.S. Pat. No. 6,147,159 ("'159 Patent") which gives a single example of a resin with methanol as its final wash. However, the resin in the '159 Patent has polyethylene glycol chains which will cause this resin to swell in methanol. Sunil et Al. (J. Comb. Chem, 2001, 3, 9–15) discloses washing with swelling solvents then with ethanol but this procedure was performed on a DVB/Styrene/vinylbenzyl chloride resin with a yield of 42% to less than 80%. The Sunil resin is not the same resin that is the subject of the present invention. Wang (J. Amer. Chem. Soc., 1973, 95, 1328–1333) discloses the washing of a functionalized 1% cross-linked resin with swelling solvents.

There also exists a significant need in the art for methods of manufacturing peptides at commercial scale using solid phase synthesis substrates made using the present invention. While various techniques are known to work at lab scale, these techniques have been found not to scale to industrial equipment well.

SUMMARY OF THE INVENTION

Applicants invention of shrinking a resin under agitation prior to drying solves the problems with free flowability encountered in the art. A further advantage is greatly increased dryer efficiency as a resin requires only 25% of its swollen volume in terms of dryer space, and there is much less solvent to remove. Further, the present invention is used on a swollen resin and leaves no residue on the beads.

The present invention provides a method for producing a free flowing resin comprising: prior to drying, shrinking the resin under agitation. Shrinking comprises charging a de-swelling solvent to a vessel. Agitation includes using one or more of the following, alone or in combination, mechanical mixing, tumbling, countercurrent charging, providing kinetic energy to the resin, lifting the resin from a resin bed using pneumatic or vibrational devices, fluidizing the resin, expanding a resin bed, and/or charging solvent in from a bottom of a resin bed into the resin. In one variant, the vessel includes a filter. In one variant of the invention, the is a resin used in solid phase synthesis of peptides.

In another aspect the invention provides a process of making a peptide using the free flowing resin described herein, and a polypeptide made using the process. Various therapeutics can then be made using the polypepdite.

In yet another aspect, the invention provides a method of making a resin product in which there is substantial bead to bead uniformity. The method includes contacting a non-packed resin bed with a non-swelling solvent. The resin is dispersed in a swelling solvent, and the method allows one to obtain a reduced volume resin product. Moreover, the method includes drying the reduced volume resin product obtained in the step above. Moreover, the resin is non-clumping.

In another aspect the present invention relates to a method for producing free flowing resin comprising the steps of contacting a resin dispersed in a swelling solvent and subsequently adding a non-swelling solvent to the dispersed resin obtain a resin that is reduced in volume; and, drying the reduced volume resin obtained above.

DETAILED DESCRIPTION OF THE INVENTION

The practice of the present invention requires adding a non-swelling solvent to a swollen resin. Non swelling solvents useful in the practice of the present invention for non polar polystyrene resins include, but are not limited to, methanol, hexane, cyclohexane, heptane, acetonitrile, ethanol, pentane, isopropanol and water and mixtures thereof. Non swelling solvents are methanol, hexane, and ethanol.

Non swelling solvents useful in the practice of the present invention for PEG functionalized polystyrene resins include, but are not limited to, octane, pentane, cyclohexane, hexane, heptane, methyl-t-butylether (MTBE), t-butanol, and ethanol.

The resins useful in the practice of the present invention which are amenable to swelling are non polar polystyrene resins including but not limited to, styrene DVB copolymers, styrene crosslinked with ester linkages, and styrene crosslinked with ether linkages. Styrene DVB copolymers functionalized with PEG are also useful in the practice of the present invention.

The reduction in volume after addition of the non swelling solvent can be in several different ranges, by way of example, 50–90%, 60–80% and 65–70%.

As used here in, the terms "dispersing" or "dispersion" or dispersed" mean fluidizing resin in a liquid. This can accomplished by means of mechanical agitation, or liquid or air flow with enough force to lift the resin from the bottom of the vessel containing the mixture and allowing the resin beads to mix freely or substantially freely.

Certain resins swell when placed in certain solvents. For example, solvents which swell non polar polystyrene resins include, but are not limited to, tetrahydrofuran (THF), dichloromethane (DCM), chloroform, dichloroethane (EDC), dioxane, N,N-dimethylformamide (DMF), n-methylpyrolidinone (NMP) and toluene and mixtures thereof.

Swelling solvents which swell PEG functionalized styrene DVB (divinylbenzene) resins include, but are not limited to, THF and N,N-dimethylformamide (DMF), acetic acid, trifluoroacetic acid, THF/water mixtures, nitromethane and mixtures thereof. Solvents include THF/Water, acetic acid, acetonitrile and Trifluoroacetic acid.

The following non limiting examples illustrate the practice of the present invention.

EXAMPLE 1

The following example illustrates the use of methanol in the invention yielding a substantially free flowing product. A slurry of approximately 59 kg polymer bound (1% DVB/Styrene) 2'chlorobenzophenone in 442 L of THF was contained in a neutche filter. The resin bed was allowed to settle and the THF was drained to 2 inches above resin level. The resin solvent mixture was then agitated to fully disperse resin in the solvent and 275 L of methanol was added while agitating, mixing was continued for 15 minutes. Resin bed is allowed to settle then drained to top of resin level. 92 L of Methanol was then added and the mixture was agitated for 15 minutes then drained completely. Nitrogen was passed through the bed to completely drain. The resin was then dried in 35° C. vacuum oven to a constant weight. A free flowing product was obtained which has similar free-flow characteristics to the free-flow characteristics of water.

COMPARATIVE EXAMPLE 2

This example illustrates a comparative process which does not give free a free-flowing product. A slurry of Approx 28 kg polymer bound (1% DVB/Styrene) 2'chlorobenzophenone in 210 L of THF was contained in a neutche filter. The resin was allowed to settle and the THF was drained. 210 L of methanol was added and drained through the resin bed. Another 210 L of methanol was added at the same rate as the effluent is being removed from the filter. Agitation was started, the resin was in big clumps which only partially broke up. The filter was drained completely. 105 L of methanol was added. Agitation was started and again big clumps of resin were noted, the resin was stirred for 15 minutes and drained completely. Vacuum was applied to remove excess solvent. The resin was dried in a 35° C. vacuum oven to a constant weight. A free flowing resin free of clumps was not obtained.

EXAMPLE 3

The follow example describes a process using hexane which gives a free flowing CTC-resin. A slurry of approximately 55 kg polymer bound (1% DVB/Styrene) 2'chlorotrityl chloride in 330 L of toluene was contained in a neutche filter. The resin bed was allowed to settle and the toluene was drained to 2 inches above resin level. The resin solvent mixture was then agitated to fully disperse resin in the solvent and 227 L of hexane was added while agitating. Mixing was continued for 15 minutes. The resin bed was allowed to settle then drained to top of resin level. 87 L of hexane was then added to the top of resin bed, agitated for 15 minutes then drained to the top of the resin bed. This step can optionally be repeated. Nitrogen was passed through the bed to completely drain. The resin was then dried in 35° C. vacuum oven to a constant weight. A product was obtained which has free flowing characteristics similar to the free flow characteristics of water.

EXAMPLE 4

This example illustrates a process using isopropyl alcohol (IPA) which gives free flowing Leucine loaded CTC-resin. The invention is also useful for amino acid loaded solid surface substrates and resins. A slurry of Approx 10 g polymer bound (1% DVB/Styrene) FMOCLeucine loaded 2'chlorotrityl chloride in 55 mL of DMF was contained in a buchner filter. The resin bed was allowed to settle and the DMF was drained to just above resin level. The resin solvent mixture was then agitated to fully disperse resin in the solvent and 55 mL of IPA was added while agitating, mixing was continued for 15 minutes. Resin bed is allowed to settle then drained to top of resin level. 55 mL of IPA was then added to the top of resin bed, agitated for 15 minutes then drained to the top of the resin bed. This step can optionally be repeated one or more times. Nitrogen was passed through the bed to completely drain. The resin was then dried in 35° C. vacuum oven to a constant weight. A product exhibiting excellent non-clumping, free-flowing characteristics which make the product suitable for re-packaging applications from bulk to smaller containers.

COMPARATIVE EXAMPLE 5

The example illustrates a comparative process which does not produce desirable free-flow characteristics. The process uses isopropyl alcohol which does not give free flowing Leucine loaded CTC-resin. A slurry of Approx 10 g polymer bound (1% DVB/Styrene) FMOCLeucine loaded 2'chlorotrityl chloride in 55 mL of DMF was contained in a buchner filter. The resin bed was allowed to settle and the DMF was drained completely. 55 mL of IPA was added without agitating, mixing was started and continued for 15 minutes. Resin bed is allowed to settle then drained completely. 55 mL of IPA was then added to the top of resin bed, agitated for 15 minutes then drained completely. 55 mL of IPA was then added to the top of resin bed, agitated for 15 minutes then drained completely. Nitrogen was passed through the bed to completely drain. The resin was then dried in 35° C. vacuum oven to a constant weight. A clumpy, non-free flowing product was obtained.

EXAMPLE 6

Place 1% DVB/Styrene resin/THF slurry into a buchner funnel, allow bed to settle and THF to drain to resin level. Add 1 bed volume (BV) of THF to top of resin bed. Allow to plug flow drain. Add 1 BV of THF and re-suspend resin. Repeat step #2. Add 1 bed volume (BV) of THF and agitate resin solvent mixture to fully disperse resin in the solvent then add 1 BV of methanol while agitating and start draining. Add another BV of methanol at the same rate as the effluent is being removed from the filter. Allow bed to settle upon at the end of the addition. Add 1 BV of Methanol to top of resin bed. Allow to plug flow drain. Add 1 BV of methanol and re-suspend resin then drain completely. Apply minimal vacuum to remove excess solvent. Dry resin in a 35° C. vacuum oven to a constant weight.

EXAMPLE 7

Place polymer bound (1% DVB/Styrene copolymer) 2'chlorotrityl chloride resin in a Buchner funnel, swept with Nitrogen to minimize contact with air. Rinse with DCM. Allow resin to drain to level. Add 1 BV of DCM and allow to plug flow drain to level. Add 1 BV of DCM and agitate resin solvent mixture to fully disperse resin in solvent then add 1 BV of anhydrous hexane while agitating and start draining. Add another BV of anhydrous hexane at the same rate as the effluent is being removed from the filter. Allow bed to settle upon at the end of the addition. Add 1 BV of anhydrous hexane and re-suspend resin. Allow to drain to level. Repeat Step #4. Apply nitrogen minimal pressure to funnel to remove excess solvent. Dry resin in a 35° C. vacuum oven and back fill with nitrogen when complete.

An exemplary "amino acid" that can be used with the resins described in the present invention, and loaded on the resin, is a compound represented by $NH_2$-CHR—COOH, wherein R is H, an aliphatic group, a substituted aliphatic group, an aromatic group or a substituted aromatic group. A "naturally-occurring amino acid" is found in nature. Examples include alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine. R is the side-chain of the amino acid. Examples of naturally occurring amino acid side-chains include methyl (alanine), isopropyl (valine), sec-butyl (isoleucine), $-CH_2CH(-CH)_2$ (leucine), benzyl (phenylalanine), p-hydroxybenzyl (tyrosine), $-CH_2OH$ (serine), $CHOHCH_3$ (threonine), $-CH_2$-3-indoyl (tryptophan), $-CH_2COOH$ (aspartic acid), $CH_2CH_2COOH$ (glutamic acid), $-CH_2C(O)NH_2$ (asparagine), $-CH_2CH_2C(O)NH_2$ (glutamine), $-CH_2SSH$ (cysteine), $-CH_2CH_2SCH_3$ (methionine), $-(CH_2)_4NH_2$ (lysine), $-(CH_2)_3NH_2$ (ornithine), $-[(CH)_2]_4NHC(=NH)NH_2$ (arginine) and $-CH_2$-3-imidazoyl (histidine). The side-chains of alanine, valine, leucine and isoleucine are aliphatic, i.e., contain only carbon and hydrogen, and are each referred to herein as "the aliphatic side chain of a naturally occurring amino acid."

The side chains of other naturally-occurring amino acids that can be used in the present invention include a heteroatom-containing functional group, e.g., an alcohol (serine, tyrosine, hydroxyproline and threonine), an amine (lysine, ornithine, histidine and arginine), a thiol (cysteine) or a carboxylic acid (aspartic acid and glutamic acid). When the heteroatom-containing functional group is modified to include a protecting group, the side-chain is referred to as the "protected side-chain" of an amino acid.

The selection of a suitable protecting group depends upon the functional group being protected, the conditions to which the protecting group is being exposed and to other functional groups which may be present in the molecule. Suitable protecting groups for the functional groups discussed above are described in Greene and Wuts, "Protective Groups in Organic Synthesis", John Wiley & Sons (1991), the entire teachings of which are incorporated into this application by reference as if fully set forth herein. The skilled artisan can select, using no more than routine experimentation, suitable protecting groups for use in the disclosed synthesis, including protecting groups other than those described below, as well as conditions for applying and removing the protecting groups.

Examples of suitable alcohol protecting groups include benzyl, allyl, trimethylsilyl, tert-butyldimethylsilyl, acetate, and the like. Examples of suitable amino protecting groups include benzyloxycarbonyl, tert-butoxycarbonyl, tert-butyl, benzyl and fluorenylmethyloxycarbonyl (Fmoc). Tert-butoxycarbonyl is an amine protecting group. Examples of suitable carboxylic acid protecting groups include tert-butyl, trityl, methyl, methoxylmethyl, trimethylsilyl, benzyloxymethyl, tert-butyldimethylsilyl and the like. Tert-butyl is a carboxylic acid protecting group. Examples of suitable thiol protecting groups include S-benzyl, S-tert-butyl, S-acetyl, S-methoxymethyl, S-trityl and the like.

Lysine, aspartate and threonine are examples of amino acid side-chains that are protected in one variant of the invention. Aliphatic groups include straight chained, branched C.sub.1–C.sub.8, or cyclic C.sub.3–C.sub.8 hydrocarbons which are completely saturated or which contain one or more units of unsaturation. In one example, an aliphatic group is a C1–C4 alkyl group. Aromatic groups include carbocyclic aromatic groups such as phenyl, 1-naphthyl, 2-naphthyl, 1-anthracyl and 2-anthracyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aromatic groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, 3-isoindolyl, and acridintyl.

Suitable substituents for an aryl group and aliphatic group are those which are compatible with the disclosed reactions, i.e., do not significantly reduce the yield of the reactions and do not cause a significant amount of side reactions. Suitable substituents generally include aliphatic groups, substituted aliphatic groups, aryl groups, halogens, halogenated alkyl groups (e.g., trihalomethyl), nitro, nitrile, —CONHR, —CON(R).sub.2, —OR, —SR, —S(O)R, —S(O).sub.2R, wherein each R is independently an aliphatic group, or an aryl group. Although certain functional groups may not be compatible with one or more of the disclosed reactions, these functional groups may be present in a protected form. The protecting group can then be removed to regenerate the original functional group. Skilled artisan will be able to select, using no more than routine experimentation, protecting groups which are compatible with the disclosed reactions.

A peptide mimetic, or component thereof, can also be used in the present invention, loaded onto a resin as described herein, or created by the process described herein. A peptide mimetic is a compound which has sufficient structural similarity to a peptide so that the desirable properties of the peptide are retained by the mimetic. For example, peptide mimetics used as protease inhibitors for treating HIV infection, are disclosed in Tung, et al., WO 94/05639, Vazquez, et al., WO 94/04491, Vazquez, et al., WO 94/10134 and Vaquez, et al., WO 94/04493. To be useful as a drug, a peptide mimetic should retain the biological activity of a peptide, but also have one or more properties which are improved compared with the peptide which is being mimicked. For example, some peptide mimetics are resistant to hydrolysis or to degradation in vivo. One strategy for preparing a peptide mimetic is to replace one or more amino acid residues in a peptide with a group which is structurally related to the amino acid residue(s) being replaced and which can form peptide bonds.

The development of new amino acid derivatives which can be used to replace amino acid residues in peptides will advance the development of new peptide mimetic drugs.

Exemplary peptide mimetics are described in U.S. Patent Application Serial No. 20020188135 by Gabriel, Richard L. et al. filed on Dec. 12, 2002 entitled, "Amino acid derivatives and methods of making the same." Also useful in one variant of the present invention are physiologically acceptable salts of these compounds. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The present invention produces a resin and/or amino acid loaded resin that is also useful in the creation and manufacture of therapeutic agents and biologically active substances that have one or more peptides, peptide derivatives, or peptide mimetics as building blocks or constituents thereof. Compounds or fragments of a compound which are terminated with an ester functionality can also be created by the present invention. The therapeutic agent that can be manufactured or created using the invention can vary widely with the purpose for the composition. The agent(s) may be described as a single entity or a combination of entities. The delivery system is designed to be used with therapeutic agents having high water-solubility as well as with those having low water-solubility to produce a delivery system that has controlled release rates. The terms "therapeutic agent" and "biologically active substance" include without limitation, medicaments; vitamins; mineral supplements; substances used for the treatment, prevention, diagnosis.

A resin useful in the present invention for making polypeptides is a CTC resin (or other type of halogenated resin). This is resin can have functionality biased toward the surface of the resin. The surface bias of the functionality places the linker group closer to the surface of the resin where it can provide better accessibility to the growing peptide chains. The surface bias is created by loading the linker to the resin under controlled swell conditions. By contacting the functionalizing reagents with the resin in a non fully swollen state, the linker is located in more sterically accessible areas of the bead. This process is described in more detail in U.S. Provisional Patent Application, by Bohling et al., filed Aug. 16, 2002, Ser. No.: 60/404,044, entitled: RESIN FOR SOLID PHASE SYNTHESIS (DN A01407). The resin is optionally loaded with an amino acid or amino acid derivative, to create one or more T-20 or T-1249 fragments.

By way of example, the present invention uses a crosslinked polymer bead which, when: (i) functionalized with a 2-chlorotrityl chloride group; (ii) coupled with Leu to 0.65 mmol/g; and (iii) coupled with Glu(t-Bu); allows coupling of FMOC-Lys(BOC)-OH at an amount of 1.5 equivalents in the presence of 1.5 equivalents of HOBT, 1.5 equivalents of DIEA and 1.5 equivalents of HBTU, to be completed, as determined by the Kaiser test, in no more than 35 minutes.

Percentages are weight percentages, unless specified otherwise. As used herein the term "(meth)acrylic" refers to acrylic or methacrylic. The term "vinyl monomer" refers to a monomer suitable for addition polymerization and containing a single polymerizable carbon-carbon double bond. The term "styrene polymer" indicates a copolymer polymerized from a vinyl monomer or mixture of vinyl monomers containing at least 50 weight percent, based on the total monomer weight, of styrene monomer, along with at least one crosslinker. Preferably a styrene polymer is made from a mixture of monomers that is at least 75% styrene, more preferably at least 90% styrene, and most preferably from a mixture of monomers that consists essentially of styrene and at least one vinylaromatic crosslinker. The polymeric bead used as a starting material in this invention contains monomer residues from at least one monomer having one copolymerizable carbon-carbon double bond and at least one crosslinker. The monomer residues derived from the crosslinker are from 0.5 mole percent to 3.0 mole percent based on the total of all monomer residues. Preferably the amount of crosslinker is from 0.7 to 1.3 mole percent, more preferably from 0.7 to 1.2 mole percent, and most preferably from 0.8 to 1.2 mole percent.

Crosslinkers are monomers having 2 or more copolymerizable carboncarbon double bonds per molecule, such as: divinylbenzene, divinyltoluene, divinylxylene, trivinylbenzene, trivinylcyclohexane, divinylnaphthalene, trivinylnaphthalene, diethyleneglycol divinylether, ethyleneglycol dimethacrylate, polyethyleneglycol dimethacrylate, triethyleneglycol dimethacrylate, trimethylolpropane trimethacrylate, allyl methacrylate, 1,5-hexadiene, 1,7-octadiene or 1,4-bis(4-vinylphenoxy)butane; it is understood that any of the various positional isomers of each of the aforementioned crosslinkers is suitable. Preferred crosslinkers are divinylbenzene, divinyltoluene, trivinylbenzene or 1,4-bis(4-vinylphenoxy)butane. The most preferred crosslinker is divinylbenzene.

Suitable monounsaturated vinylaromatic monomers that may be used in the preparation of the bead used as a starting material in the present invention include, for example, styrene, α-methylstyrene, ($C_1$–$C_4$)alkyl-substituted styrenes and vinylnaphthalene; preferably one or more monounsaturated vinylaromatic monomer is selected from the group consisting of styrene and ($C_1$–$C_4$)alkyl-substituted styrenes. Included among the suitable ($C_1$–$C_4$)alkyl-substituted styrenes are, for example, ethylvinylbenzenes, vinyltoluenes, diethylstyrenes, ethylmethylstyrenes, dimethylstyrenes and isomers of vinylbenzyl chloride; it is understood that any of the various positional isomers of each of the aforementioned vinylaromatic monomers is suitable.

Optionally, non-aromatic vinyl monomers, such as aliphatic unsaturated monomers, for example, acrylonitrile, glycidyl methacrylate, (meth)acrylic acids and amides or $C_1$–$C_6$ alkyl esters of (meth)acrylic acids may also be used in addition to the vinylaromatic monomer. When used, the non-aromatic vinyl monomers typically comprise as polymerized units, from zero to 20%, preferably from zero to 10%, and more preferably from zero to 5% of the copolymer, based on the total monomer weight used to form the copolymer.

Preferred vinyl monomers are the vinylaromatic monomers; more preferably styrene, isomers of vinylbenzyl chloride, and α-methylstyrene. The most preferred vinyl monomer is styrene.

Optionally, the preparation of the beads may include an enzyme treatment to cleanse the polymer surface of residues of dispersants and suspending agents used during the polymerization. The enzyme treatment typically involves contacting the polymeric phase with the enzymatic material (selected from one or more of cellulose-decomposing enzyme and proteolytic enzyme) during polymerization, following polymerization or after isolation of the polymer. Japanese Patent Applications No. 61-141704 and No. 57-98504 may be consulted for further general and specific details on the use of enzymes during the preparation of polymer resins. Suitable enzymes include, for example, cellulose-decomposing enzymes, such as β-1,4-glucan-4-glucano-hydrase, β-1,4-glucan-4-glucanhydrolase, β-1,4-glucan-4-glucohydrase and β-1,4-glucan-4-cellobiohydrase, for cellulose-based dispersant systems; and proteolytic enzymes, such as urokinase, elastase and enterokinase, for gelatin-based dispersant systems. Typically, the amount of enzyme used relative to the polymer is from 2 to 35%, preferably from 5 to 25% and more preferably from 10 to 20%, based on total weight of polymer.

A functionalizing reagent is one which covalently attaches a functional group to the polymer comprising the bead. Further elaboration of the functional group may be necessary to maximize the utility of the bead as a support for solid phase synthesis. However, the initial attachment of the functional group determines the region of the bead which is functionalized and thus tends to control the ability of the bead to react with substrates for solid phase synthesis and to allow recovery of the synthetic product. For styrene polymers, the functionalization typically is a Friedel-Crafts substitution on the aromatic ring, preferably an acylation, bromination, or halomethylation. Subsequent elaboration of the initial functional group typically is done. For example, acylation by aroyl halides often is followed by addition of an aryl lithium to the carbonyl group of the product to produce a triaryl carbinol functional group, which then is halogenated to produce a trityl halide functional group. In one preferred embodiment of the invention, 2-chlorobenzoyl chloride, followed by phenyllithium, and then thionyl chloride, produces a 2-chlorotrityl chloride functional group. Bromination typically is followed by treatment with an alkyl lithium reagent and reaction of the aryl lithium product with a variety of reagents to produce different functional groups. Halomethyl groups also may react with a variety of reagents to produce different functional groups.

In yet another variant, the invention provides an improved process for making a T-20 or a T-1249 composition, or a fragment of a T-20 or a T-1249 composition using a low void space resin optionally loaded with an amino acid or amino acid derivative to create one or more T-20 or T-1249 fragments.

Precursor resins that can be made free flowing using the novel methods herein can be made by (a) preparing bead copolymer with composed from: (i) a monomer mixture comprising at least one vinyl monomer and at least one crosslinker; and (ii) from 0.25 mole percent to 1.5 mole percent of at least one free radical initiator; (b) allowing the monomer mixture to polymerize; and (c) washing the bead with an aprotic organic solvent. Of course, it is appreciated that other methods can also be used to obtain the resins used in the present invention.

As used herein the term "(meth)acrylic" refers to acrylic or methacrylic. The term "vinyl monomer" refers to a monomer suitable for addition polymerization and containing a single polymerizable carbon-carbon double bond. The term "styrene polymer" indicates a copolymer polymerized from a vinyl monomer or mixture of vinyl monomers containing at least 50 weight percent, based on the total monomer weight, of styrene monomer, along with at least one crosslinker. Preferably a styrene polymer is made from a mixture of monomers that is at least 75% styrene, more preferably at least 90% styrene, and most preferably from a mixture of monomers that consists essentially of styrene and at least one vinylaromatic crosslinker. The lightly crosslinked polymeric bead of this invention contains monomer residues from at least one monomer having one copolymerizable carbon-carbon double bond and at least one crosslinker. The monomer residues derived from the crosslinker are from 0.5 mole percent to 2 mole percent based on the total of all monomer reisdues.

A polymeric bead is a spherical copolymer bead having a particle diameter no greater than 800 microns (μm), preferably no greater than 170 μm, more preferably no greater than 150 μm, more preferably no greater than 125 μm, and most preferably no greater than 100 μm.

The polymeric bead used in the present invention preferably is produced by a suspension polymerization or seed expansion. A typical bead preparation, for example, may include preparation of a continuous aqueous phase solution containing typical suspension aids, for example, dispersants, protective colloids and buffers. Preferably, to aid in production of the relatively small beads of the present invention, a surfactant is included in the aqueous solution, preferably a sodium alkyl sulfate surfactant, and vigorous agitation is maintained during the polymerization process. The aqueous solution is combined with a monomer mixture containing at least one vinyl monomer, at least one crosslinker and at least one free-radical initiator. Preferably, the total initiator level is from 0.25 mole percent to 1.5 mole %, based on the total monomer charge, preferably from 0.4 mole percent to 1 mole percent, more preferably from 0.4 mole percent to 0.8 mole percent, and most preferably from 0.5 mole percent to 0.7 mole percent. The mixture is purged of most of the oxygen by introducing an inert gas until the oxygen level in the atmosphere in the reaction vessel (head space) is less than 5%, preferably less than 3%, more preferably less than 2%, and most preferably less than 1%. Preferably, the inert gas is introduced into the aqueous solution and the monomer mixture, as well as the head space. The mixture of monomers is then polymerized at elevated temperature. Preferably, the polymerization is continued for a time sufficient to reduce the unreacted vinyl monomer content to less than 1% of the starting amount. The resulting bead is then isolated by conventional means, such as dewatering, washing with an aprotic organic solvent, and drying.

Crosslinkers are monomers having 2 or more copolymerizable carbon-carbon double bonds per molecule, such as: divinylbenzene, divinyltoluene, divinylxylene, trivinylbenzene, trivinylcyclohexane, divinylnaphthalene, trivinylnaphthalene, diethyleneglycol divinylether, ethyleneglycol dimethacrylate, polyethyleneglycol dimethacrylate triethyleneglycol dimethacrylate, trimethylolpropane trimethacrylate, allyl methacrylate, 1,5-hexadiene, 1,7-octadiene or 1,4-bis(4-vinylphenoxy)butane; it is understood that any of the various positional isomers of each of the aforementioned crosslinkers is suitable. Preferred crosslinkers are divinylbenzene, divinyltoluene, trivinylbenzene or 1,4-bis(4-vinylphenoxy)butane. The most preferred crosslinker is divinylbenzene.

Suitable monounsaturated vinylaromatic monomers that may be used in the preparation of the bead used in the present invention include, for example, styrene, α-methylstyrene, ($C_1$–$C_4$)alkyl-substituted styrenes and vinylnaphthalene; preferably one or more monounsaturated vinylaromatic monomer is selected from the group consisting of styrene and ($C_1$–$C_4$)alkyl-substituted styrenes. Included among the suitable ($C_1$–$C_4$)alkyl-substituted styrenes are, for example, ethylvinylbenzenes, vinyltoluenes, diethylstyrenes, ethylmethylstyrenes, dimethylstyrenes and isomers of vinylbenzyl chloride; it is understood that any of the various positional isomers of each of the aforementioned vinylaromatic monomers is suitable.

Optionally, non-aromatic vinyl monomers, such as aliphatic unsaturated monomers, for example, acrylonitrile, glycidyl methacrylate, (meth)acrylic acids and amides or $C_1$–$C_6$ alkyl esters of (meth)acrylic acids may also be used in addition to the vinylaromatic monomer. When used, the non-aromatic vinyl monomers typically comprise as polymerized units, from zero to 20%, preferably from zero to 10%, and more preferably from zero to 5% of the copolymer, based on the total monomer weight used to form the copolymer.

Preferred vinyl monomers are the vinylaromatic monomers; more preferably styrene, isomers of vinylbenzyl chloride, and α-methylstyrene. The most preferred vinyl monomer is styrene.

Polymerization initiators useful preparing the beads used in the present invention include monomer-soluble initiators such as peroxides, hydroperoxides, peroxyesters and related initiators; for example benzoyl peroxide, tert-butyl hydroperoxide, cumene peroxide, tetralin peroxide, acetyl peroxide, caproyl peroxide, tert-butyl peroctoate (also known as tert-butylperoxy-2-ethylhexanoate), tert-amyl peroctoate, tert-butyl perbenzoate, tert-butyl diperphthalate, dicyclohexyl peroxydicarbonate, di(4-tert-butylcyclohexyl) peroxydicarbonate and methyl ethyl ketone peroxide. Also useful are azo initiators such as azodiisobutyronitrile, azodiisobutyramide, 2,2'-azo-bis(2,4-dimethylvaleronitrile), azo-bis(α-methyl-butyronitrile) and dimethyl-, diethyl- or dibutyl azo-bis(methylvalerate). Preferred peroxide initiators are diacyl peroxides, such as benzoyl peroxide, and peroxyesters, such as tert-butyl peroctoate and tert-butyl perbenzoate.

Optionally, the preparation of the beads may include an enzyme treatment to cleanse the polymer surface of residues of dispersants and suspending agents used during the polymerization. The enzyme treatment typically involves contacting the polymeric phase with the enzymatic material (selected from one or more of cellulose-decomposing enzyme and proteolytic enzyme) during polymerization, following polymerization or after isolation of the polymer. Japanese Patent Applications No. 61-141704 and No. 57-98504 may be consulted for further general and specific details on the use of enzymes during the preparation of polymer resins. Suitable enzymes include, for example, cellulose-decomposing enzymes, such as β-1,4-glucan-4-glucano-hydrase, β-1,4-glucan-4-glucanhydrolase, β-1,4-glucan-4-glucohydrase and? β-1,4-glucan-4-cellobiohydrase, for cellulose-based dispersant systems; and proteolytic enzymes, such as urokinase, elastase and enterokinase, for gelatin-based dispersant systems. Typically, the amount of enzyme used relative to the polymer is from 2 to 35%, preferably from 5 to 25% and more preferably from 10 to 20%, based on total weight of polymer.

The examples below show exemplary peptide builds. The results of this example are shown in table 4. It is appreciated that various combinations of peptide builds can be constructed using the techniques described herein.

It is appreciated that the methods described herein can be used for very low cost and efficient synthesis of peptides, in particular T-20, and T-20-like peptides. Such methods utilize solid and liquid phase synthesis procedures to synthesize and combine groups of specific peptide fragments to yield the peptide of interest. In other variant, individual peptide fragments which act as intermediates in the synthesis of the peptides of interest (e.g., T-20) are also created. In yet another aspect the present invention provides for the creation of groups of such peptide intermediate fragments which can be utilized together to produce full length T-20 and T-20-like peptides.

In another aspect, the peptides or fragments of peptides created by the processes described herein are purified, and/or the individual peptide fragments which act as intermediates in the synthesis of the subject peptides are also purified.

It is further appreciated that the invention can also be used to create peptides and peptide fragments which exhibit an ability to inhibit fusion-associated events, and, importantly, also exhibit potent antiviral activity. These peptides and peptide fragments are described in U.S. Pat. Nos. 5,464,933; 5,656,480 and PCT Publication No. WO 96/19495, incorporated by reference herein as expressly set forth. The invention provides a method for creating these therapeutics in large scale quantities.

T-20 and T-20 fragments are made using solid and liquid phase synthesis procedures to synthesize and combine groups of specific peptide fragments to yield the peptide of interest. Generally, the methods of the invention include synthesizing specific side-chain protected peptide fragment intermediates of T-20 or a T-20-like peptide on a solid support created by the invention described herein, coupling the protected fragments in solution to form a protected T-20 or T-20-like peptide, followed by deprotection of the side chains to yield the final T-20 or T-20-like peptide. A preferred embodiment of the methods of the invention involves the synthesis of a T-20 peptide having an amino acid sequence as depicted in U.S. Pat. No. 6,015,881 ("'881 Patent").

The present invention further relates to individual peptide fragments which act as intermediates in the synthesis of the peptides of interest (e.g., T-20). The peptide fragments of the invention include, but are not limited to, those having amino acid sequences as described in the '881 Patent.

It is appreciated that the present invention can also create one or more peptide fragments using conventional techniques using CTC-resins, and create one or more peptide fragments using the techniques described herein using the alcohol based resins as described in our patent application filed Feb. 12, 2003 by Bohling et al., entitled "AMINO ACID LOADED TRITYL ALCOHOL RESINS, METHOD OF PRODUCTION OF AMINO ACID LOADED TRITYL ALCOHOL RESINS, AND BIOLOGICALLY ACTIVE SUBSTANCES AND THERAPEUTICS PRODUCED THEREWITH" docket no. DN A01485. The resulting peptides can thereafter be combined to obtain the T-20 peptides or T-20 like peptides.

It will be understood that the methods, fragments and groups of fragments and techniques utilized for choosing the fragments and groups of fragments of the present invention may be used to synthesize T-20-like fragments in addition to T-20. The term "T-20-like" as used herein means any HIV or non-HIV peptide listed in U.S. Pat. Nos. 5,464,933; 5,656,480 or PCT Publication No. WO 96/19495, each of which is hereby incorporated by reference in its entirety.

In addition to T-20 and the T-20-like peptides described above, the methods, fragments and groups of fragments of the present invention may be used to synthesize peptides having modified amino and/or carboxyl terminal ends.

In a preferred embodiment, the methods of the invention are used to synthesize the peptide having a formula wherein X is an acetyl group and Z is an amide group. In a preferred method, T-20 and T-20-like peptides and intermediates can be purified using any non-silica based column packing (for maximization of loading capacity) including but not limited to zirconium-based packings, poly-styrene, poly-acrylic or other polymer based packings which are stable at high (greater than >7) pH ranges. For example, among the non-silica-laded column packing exhibiting a broad pH range that includes pH valves greater than that are sold by Tosohaus (Montgomeryville, Pa.). Columns packed with such material can be run in low, medium or high pressure chromatography The present invention also provides for large scale efficient production of peptide fragment intermediates of T-20 and T-20-like peptides with specific amino acid sequences as listed in Table 1 above of the '881 Patent, and the groups of peptide fragment intermediates listed in Table 2 of the '881 Patent. Such peptide intermediates, especially in groups as listed in Table 2 of the '881 Patent are utilized to produce T-20 and T-20 like peptides.

Any one or more of the side-chains of the amino acid residues of peptide fragments may be protected with standard protecting groups such as t-butyl (t-Bu), trityl (trt) and t-butyloxycarbonyl (Boc). The t-Bu group is the preferred side-chain protecting group for amino acid residues Tyr(Y), Thr(T), Ser(S) and Asp(D); the trt group is the preferred side-chain protecting group for amino acid residues His(H), Gln(Q) and Asn(N); and the Boc group is the preferred side-chain protecting group for amino acid residues Lys(K) and Trp(W).

During the synthesis of fragments, the side-chain of the histidine residue is be protected, preferably with a trityl (trt) protecting group. If it is not protected, the acid used to cleave the peptide fragment from the resin may detrimentally react with the histidine residue, causing degradation of the peptide fragment.

The glutamine residues of the peptide fragments of the invention are protected with trityl (trt) groups. However, it is possible not to protect the glutamine residue at the carboxy-terminal end of certain fragments. All the asparagine residues of each peptide fragment of the invention can be protected. In addition, the tryptophan residue is protected with a Boc group.

Some of the individual peptide fragments are made using solid phase synthesis techniques described herein, while other peptides of the invention are optionally made using a combination of solid phase and solution phase synthesis techniques. The peptides of the invention may alternatively be synthesized such that one or more of the bonds which link the amino acid residues of the peptides are non-peptide bonds. These alternative non-peptide bonds may be formed by utilizing reactions well known to those in the art, and may include, but are not limited to imino, ester, hydrazide, semicarbazide, and azo bonds, to name but a few.

In yet another embodiment of the invention, T-20 and T-20 like peptides comprising the sequences described above may be synthesized with additional chemical groups present at their amino and/or carboxy termini, such that, for example, the stability, reactivity and/or solubility of the peptides is enhanced. For example, hydrophobic groups such as carbobenzoxyl, dansyl, acetyl or t-butyloxycarbonyl groups, may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini. Similarly, a para-nitrobenzyl ester group may be placed at the peptides' carboxy termini.

Preferably, one or more the peptide fragments of the present invention are synthesized by solid phase peptide synthesis (SPPS) techniques described herein using standard FMOC protocols. See, e.g., Carpino et al., 1970, J. Am. Chem. Soc. 92(19):5748–5749; Carpino et al., 1972, J. Org. Chem. 37(22):3404–3409.

The processes and substrates described herein can also be used to construct the polypeptide described in U.S. Pat. No. 6,469,136 ("'136 Patent"). In particular, peptides referred to herein as T-1249 and T-1249-like peptides can be constructed using the novel methods described herein, alone or in combination with the conventional methods described herein. These methods utilize solid and liquid phase synthesis procedures to synthesize and combine groups of specific peptide fragments to yield the peptide of interest.

Novel methods for the synthesis of peptides, in particular peptides referred to herein as T-1249 and T-1249-like peptides, are described herein. These methods utilize solid and liquid phase synthesis procedures to synthesize and combine groups of specific peptide fragments to yield the peptide of interest. Generally, the methods include synthesizing specific side-chain protected peptide fragment intermediates of T-1249 or a T-1249-like peptide on a solid support, coupling the protected fragments in solution to form a protected T-1249 or T-1249-like peptide, followed by deprotection of the side chains to yield the final T-1249 or T-1249-like peptide. A preferred embodiment of the methods of the invention involves the synthesis of a T-1249 peptide having an amino acid sequence as depicted in the '136 Patent.

The present invention further provides a low cost, highly efficient method to construct individual peptide fragments which act as intermediates in the synthesis of the peptides of interest (e.g., T-1249). The peptide fragments of the invention include, but are not limited to, those having amino acid sequences as depicted in Table 1 of the '136 Patent. Combinations of solid phase liquid phase synthetic reactions as described herein allow high purity T-1249 and T-1249-like peptides to be manufactured for on a large scale with higher throughput and higher yield than those described in the art. T-1249 and T-1249-like peptides may be synthesized on a scale of one or more kilograms.

The present invention is used to synthesize the peptide known as T-124. T-1249 is a 39 amino acid residue polypeptide whose sequence is derived from HIV-1, HIV-2 and SIV gp41 viral polypeptide sequences. It will be understood that the methods, fragments and groups of fragments and techniques utilized for choosing the fragments and groups of fragments of the present invention may be used to synthesize T-1249-like fragments in addition to T-1249. The term "T-1249-like" as used herein means any HIV or non-HIV peptide listed in International Application No. PCT/US99/11219, filed May 20, 1999, International Publication No. WO 99/59615 published Nov. 25, 1999.

In addition to T-1249 and the T-1249-like peptides described above, the methods, fragments and groups of fragments of the present invention may be used to synthesize peptides having modified amino and/or carboxyl terminal ends or other polymer based packings which are stable at high and low pH ranges.

One or more peptide fragment intermediates of T-1249 and T-1249-like peptides with specific amino acid sequences as listed in Table 1 of the '136 Patent, and one or more groups of peptide fragment intermediates listed in Table 2 of the '136 Patent are also constructed using the novel processes described herein, alone or in combination with other art processes.

Peptide Synthesis

Individual peptide fragments are preferably made using solid phase synthesis techniques, while other peptides of the invention are optionally made using a combination of solid phase and solution phase synthesis techniques. The syntheses culminate in the production of T-1249 or T-1249-like peptides.

The peptides of the invention may alternatively be synthesized such that one or more of the bonds which link the amino acid residues of the peptides are non-peptide bonds. These alternative non-peptide bonds may be formed by utilizing reactions well known to those in the art, and may include, but are not limited to imino, ester, hydrazide, semicarbazide, and azo bonds, to name but a few. Further, T-1249 and T-1249-like peptides may be synthesized such that their steric configuration is altered. For example, the D-isomer of one or more of the amino acid residues of the peptide may be used, rather than the usual L-isomer.

Still further, at least one of the amino acid residues of the peptides of the invention may be substituted by one of the well known non-naturally occurring amino acid residues. Alterations such as these may serve to increase the stability, reactivity and/or solubility of the peptides of the invention. Any of the T-1249 or T-1249-like peptides may be synthesized to additionally have a macromolecular carrier group covalently attached to its amino and/or carboxy termini. Such macromolecular carrier groups may include, for example, lipid-fatty acid conjugates, polyethylene glycol, carbohydrates or additional peptides.

Method for Solid Phase Peptide Synthesis (SPPS); General Procedure

A SPPS chamber is charged with free-flowing FmocLeu-resin (1 eq). The resin is conditioned in 5% piperidine DCM (7.5 vol) with a nitrogen purge for 15–30 minutes. The solvent is drained and the resin is treated with 2.times.20% piperidine in NMP (5 volumes) for 30 minutes to remove the Fmoc protecting group. After the second 20% piperidine/NMP treatment, the resin is washed with 5–7.times.NMP (5 vol) to a negative choranil test.

Meanwhile, the subsequent amino acid (1.5 eq), HOBT (1.5 eq) and DIEA (1.5 eq) are combined in 3:1 NMP/DCM (10 vol), allowed to fully dissolve at room temperature and cooled to 0 degrees C. HBTU is added, the solution is stirred for 10–15 minutes to dissolve the solid then added to the resin. The suspension is agitated with stirring under a nitrogen atmosphere for 1–3 hours. Coupling completion is monitored with a qualitative ninhydrin test. If the reaction is incomplete after 3 h (positive ninhydrin test persists) the reactor should be drained and a recoupling should be performed with a fresh solution of activated amino acid (0.5 eq). Normally after 30 min–1 h of recoupling a negative ninhydrin test is obtained. This cycle is repeated for the remaining amino acids in the fragment. As the fragment builds, the solvent volumes used in the washes may need to be increased from 5 volumes. Following the final coupling, the resin is washed with 3.times.5–8 volumes of NMP then 2.times.10 volumes of DCM and dried to constant weight in a vacuum oven at 40° C.

RECYCLING EXAMPLE

The resin described in this invention is recycled by removing the peptide using standard conditions, then con verted to the chlorotrityl resin with sodium hydroxide. The chlorotrityl alcohol resin is then converted to CTC by treatment with thionyl chloride and a catalytic amount of dimethyl formamide in toluene. The increased durability of the uniformly functionalized resin has lead to significantly improved perfect bead count and processability for the recycled resin compared to the resins currently found in the art.

It is further appreciated that large scale manufacture of peptides is facilitated using the non-clumping and/or free flowing resin product of the invention. The free flowing resin has properties that allow it to pass freely through components of manufacturing systems including feed tubes and funnels, permit easy repackaging of the resin from bulk containers to end user containers (i.e. lab scale containers containing in the range of 0.5 gram to several gram or kilogram quantities), allow for significant interaction of the loaded aa sites with other reactants to make polypeptides and fragments thereof, and provide for greater bead to bead uniformity than convention resins.

We claim:

1. A method for producing a free flowing resin comprising:
   i) providing a resin dispersed in a swelling solvent in a vessel,
   ii) while said resin is under agitation, adding a non-swelling solvent to said resin dispersed in a swelling solvent, and
   iii) then drying said resin,
   wherein said resin comprises a crosslinked polymer that is polymerized from monomers comprising
      a) one or more monounsaturated vinylaromatic monomers, and
      b) one or more monomers having 2 or more copolymerizable carbon-carbon double bonds per molecule.

2. The method of claim 1 in which said resin is a solid phase synthesis resin.

3. The method of claim 1 in which said adding a non-swelling solvent causes said resin to shrink.

4. The method of claim 1 in which said vessel comprises a filter.

5. The method of claim 1 in which said agitation is selected from the group consisting of mechanical mixing, tumbling, countercurrent charging, providing kinetic energy to said resin, lifting said resin from a resin bed, fluidizing said resin, expanding a resin bed, and charging solvent in from a bottom of a resin bed into said resin.

6. The method of claim 1, wherein said crosslinked polymer is polymerized from monomers comprising at least 50 weight percent, based on the total monomer weight, styrene.

7. The method of claim 1, wherein said crosslinked polymer is polymerized from monomers comprising from 0.5 to 3.0 mole percent, based on the total of all monomers, one or more monomers having 2 or more copolymerizable carbon-carbon double bonds per molecule.

* * * * *